United States Patent
Zhao et al.

(10) Patent No.: US 9,782,356 B2
(45) Date of Patent: Oct. 10, 2017

(54) CAPSULE SHELLS COMPRISING AN ESTERIFIED CELLULOSE ETHER

(71) Applicant: Dow Global Technologies LLC, Midland, MI (US)

(72) Inventors: Jin Zhao, Midland, MI (US); Roland Adden, Bomlitz (DE); Brian Koblinski, Midland, MI (US); Robert L. Schmitt, Annandale, NJ (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/308,767

(22) PCT Filed: Apr. 28, 2015

(86) PCT No.: PCT/US2015/027867
§ 371 (c)(1),
(2) Date: Nov. 3, 2016

(87) PCT Pub. No.: WO2015/179073
PCT Pub. Date: Nov. 26, 2015

(65) Prior Publication Data
US 2017/0181976 A1    Jun. 29, 2017

Related U.S. Application Data

(60) Provisional application No. 62/000,714, filed on May 20, 2014.

(51) Int. Cl.
| | |
|---|---|
| *A61K 9/48* | (2006.01) |
| *B29C 41/14* | (2006.01) |
| *B29C 41/00* | (2006.01) |
| *B29C 41/46* | (2006.01) |
| *B29K 1/00* | (2006.01) |
| *B29L 31/00* | (2006.01) |

(52) U.S. Cl.
CPC .......... *A61K 9/4816* (2013.01); *B29C 41/003* (2013.01); *B29C 41/14* (2013.01); *B29C 41/46* (2013.01); *B29K 2001/12* (2013.01); *B29L 2031/7174* (2013.01)

(58) Field of Classification Search
CPC ................................................ B29L 2031/7174
See application file for complete search history.

(56) References Cited

U.S. PATENT DOCUMENTS

| | | | |
|---|---|---|---|
| 4,226,981 | A | 10/1980 | Onda et al. |
| 4,365,060 | A | 12/1982 | Onda et al. |
| 2009/0297565 | A1 | 12/2009 | Müller |
| 2012/0016364 | A1 | 1/2012 | Mayse et al. |
| 2013/0295188 | A1 | 11/2013 | Cade et al. |

FOREIGN PATENT DOCUMENTS

| | | |
|---|---|---|
| EP | 2476439 A1 | 7/2012 |
| GB | 2325623 A | 12/1998 |
| GB | 2353215 A | 2/2001 |
| JP | 2006-016372 | 1/2006 |
| WO | 2008047201 | 4/2008 |
| WO | 2013150331 | 10/2013 |
| WO | 2013164121 A1 | 11/2013 |

*Primary Examiner* — Theodore R. West (57) ABSTRACT

A polymeric capsule shell of high quality is prepared from an aqueous composition which comprises (A) at least one esterified cellulose ether comprising aliphatic monovalent acyl groups and groups of the formula —C(O)—R—COOH, R being a divalent aliphatic or aromatic hydrocarbon group, wherein at least a part of the groups —C(O)—R—COOH are neutralized with an ammonium salt of carbonic acid, formic acid or acetic acid, and (B) from 0 to 7 weight percent of a non-polymeric plasticizer, based on the weight of the esterified cellulose ether, wherein the weight of said at least one esterified cellulose ether is at least 80 percent of the total polymer weight in the aqueous composition.

16 Claims, 3 Drawing Sheets

CAPSULE SHELLS COMPRISING AN ESTERIFIED CELLULOSE ETHER

FIELD

This invention concerns polymeric capsule shells comprising an esterified cellulose ether, a process for producing the capsule shells and capsules comprising such capsule shells.

INTRODUCTION

Esters of cellulose ethers, their uses and processes for preparing them are generally known in the art. Known methods of producing cellulose ether-esters include the reaction of a cellulose ether with an aliphatic monocarboxylic acid anhydride or a dicarboxylic acid anhydride or a combination thereof, for example as described in U.S. Pat. Nos. 4,226,981 and 4,365,060.

Various known esterified cellulose ethers are useful as enteric polymers for pharmaceutical dosage forms, such as methylcellulose phthalate (MCP), hydroxypropyl methylcellulose phthalate (HPMCP), methylcellulose succinate (MCS), or hydroxypropyl methylcellulose acetate succinate (HPMCAS). The esterified cellulose ethers are used for coating dosage forms, such as tablets, microparticulates or capsules. Enteric polymers protect the drug from inactivation or degradation in the acidic environment or prevent irritation of the stomach by the drug, but are dissolved in the intestinal canals to release the drug contained therein.

U.S. Pat. No. 4,365,060 discloses enterosoluble capsules which are said to have excellent enterosolubility behavior. The capsules are prepared from a mixed ester of an alkyl-, hydroxyalkyl- or hydroxyalkyl-alkyl-cellulose esterified with succinyl anhydride and an aliphatic monocarboxylic acid anhydride. The US patent discloses that the cellulose derivative can be shaped into capsules not only by the conventional dipping method but also by the plastic deformation at an elevated temperature under pressure such as compression molding, vacuum forming, matched-mold forming and the like. The US patent states that the enterosoluble capsules have excellent pliability, even with addition of no or a very small amount of plasticizer. Unfortunately, the dipping method requires the use of an organic solvent for dissolving the mixed ester of an alkyl-, hydroxyalkyl- or hydroxyalkyl-alkyl-cellulose. Organic solvents are often not desirable for pharmaceutical or nutritional uses. Moreover, the handling of organic solvents adds to the complexity of the process for producing the capsules. Forming capsules by plastic deformation is often not desirable either due to the significant thermal stress and thermal degradation caused by the heat that is needed for thermoforming or the complex and expensive molding process for thermoforming thin film capsules.

To overcome the above-mentioned disadvantages, US Patent Application Publication US 2012/0161364 discloses an aqueous composition for enteric hard capsules comprising an enteric base material, such as HPMCAS or HPMCP, a capsule forming aid, such as a cellulose ether, and a neutralizing agent, such as sodium hydroxide, aqueous ammonia, potassium hydroxide, or calcium hydroxide. The capsule forming aid is used at significant amounts. According to the working examples the capsules comprise at least 10 percent of a cellulose ether as a capsule forming aid, based on the total weight of the enteric polymer and the capsule forming aid, when HPMCP is used as enteric polymer. When HPMCAS is used as enteric polymer, the capsules comprise even 30 percent of a cellulose ether as a capsule forming aid, based on the total weight of the enteric polymer and the capsule forming aid. These film-forming aids are non-enteric polymers. Such large amounts of cellulose ethers as film-forming aids affect the enteric properties of the capsules. Although disintegration times of more than 120 minutes are reported at a pH of 1.2, i.e., in an acidic environment like in the stomach, release of the drug contained in the capsule can result before complete disintegration. Moreover, the capsules based on HPMCAS are reported to be hazy in US 2012/0161364.

International Patent Application WO 2013/164121 teaches that many techniques for preparing capsules still require the combination of an enteric (acid insoluble) polymer and a conventional non-enteric polymer, require salts or pH regulators leading to water sensitivity or brittleness of the resulting capsule shells, require multiple processing steps, and/or need to be processed in non-aqueous media. To solve these problems, WO 2013/164121 discloses an aqueous composition comprising HPMCAS polymer dispersed in water, wherein the polymer is partially neutralized with at least one alkaline material, such as ammonia, sodium hydroxide, calcium hydroxide, potassium hydroxide, cationic polymers, and mixtures thereof. WO 2013/164121 shows in the examples that capsules produced from these dispersions have a good or fine flexibility and a good resistance to demineralized water, i.e., the capsule dissolves after 2 hours. Unfortunately, these dispersions also comprise a large amount of the plasticizer triacetine, i.e., 10 wt.-% based on the weight of HPMCAS. Such large amount is often not desirable in capsules for pharmaceutical or nutritional uses. Moreover, WO 2013/164121 also shows that the comparative capsules prepared from aqueous dispersions of HPMCAS that is fully neutralized with $NH_3$ are brittle and have a poor resistance to demineralized water and are dissolved within less than 30 minutes. The comparative capsules are brittle even though they comprise about 25 wt.-percent of other components than HPMCAS, specifically the polymeric dispersant Tween 80, a film-forming agent HPMC, a gelling agent poloxamer, and/or the plasticizer triacetine.

Accordingly, there is still the urgent need to provide polymeric capsule shells displaying enteric properties, particularly hard capsule shells, which do not require the use of a large amount of polymeric film-forming aids or a large amount of non-polymeric plasticizers. It is one object of the present invention to provide such polymeric capsule shells. It is another object of the present invention to produce such polymeric capsule shells in an efficient manner, specifically without post-treatment of the produced capsules with one or more additional layers to impart enteric properties.

Surprisingly, it has been found that polymeric capsule shells of excellent properties can be prepared from an aqueous composition which comprises a certain esterified cellulose ether that is at least partially neutralized with a specific salt, as described further below.

SUMMARY

One aspect of the present invention is a polymeric capsule shell which comprises (A) at least one esterified cellulose ether comprising aliphatic monovalent acyl groups and groups of the formula —C(O)—R—COOH, R being a divalent aliphatic or aromatic hydrocarbon group, wherein a part of the groups —C(O)—R—COOH are neutralized with an ammonium salt of carbonic acid, formic acid or acetic acid, and (B) from 0 to 7 weight percent of a non-polymeric plasticizer, based on the weight of the esterified cellulose ether, wherein the weight of said at least one esterified cellulose ether is at least 80 percent of the total polymer weight in the capsule shell.

Another aspect of the present invention is a polymeric capsule shell that has been prepared from an aqueous composition which comprises (A) at least one esterified cellulose ether comprising aliphatic monovalent acyl groups and groups of the formula —C(O)—R—COOH, R being a divalent aliphatic or aromatic hydrocarbon group, wherein at least a part of the groups —C(O)—R—COOH are neutralized with an ammonium salt of carbonic acid, formic acid or acetic acid, and (B) from 0 to 7 weight percent of a non-polymeric plasticizer, based on the weight of the esterified cellulose ether, wherein the weight of said at least one esterified cellulose ether is at least 80 percent of the total polymer weight in the aqueous composition.

Yet another aspect of the present invention is a capsule which comprises an above-mentioned capsule shell and further comprises a drug or a nutritional or food supplement or a combination thereof.

Yet another aspect of the present invention is a process for producing polymeric capsule shells which comprises the steps of providing an aqueous composition comprising (A) at least one esterified cellulose ether comprising groups of the formula —C(O)—R—COOH, R being a divalent aliphatic or aromatic hydrocarbon group, wherein at least a part of the groups —C(O)—R—COOH are neutralized with an ammonium salt of carbonic acid, formic acid or acetic acid, and (B) from 0 to 7 weight percent of a non-polymeric plasticizer, based on the weight of the esterified cellulose ether, wherein the weight of said at least one esterified cellulose ether is at least 80 percent of the total polymer weight in the aqueous composition, dipping molding pins into the aqueous composition, forming a film on said molding pins by withdrawing said pins from said aqueous composition, and drying the film on the molding pins.

DESCRIPTION OF EMBODIMENTS

Surprisingly, it has been found that polymeric capsules and capsule shells of excellent properties can be prepared from an aqueous composition which comprises a certain esterified cellulose ether that is at least partially neutralized with an ammonium salt of carbonic acid, formic acid or acetic acid. Capsule shells of excellent quality can be produced in a simple dipping process without the need of an organic solvent and without the need of a large amount of polymeric film-forming aids or a large amount of non-polymeric plasticizers.

The one or more esterified cellulose ethers comprised in the capsules and capsule shells of the present invention have a cellulose backbone having β-1,4 glycosidically bound D-glucopyranose repeating units, designated as anhydroglucose units in the context of this invention. The esterified cellulose ether preferably is an esterified alkyl cellulose, hydroxyalkyl cellulose or hydroxyalkyl alkylcellulose. This means that in the esterified cellulose ether comprised in the capsules and capsule shells of the present invention, at least a part of the hydroxyl groups of the anhydroglucose units are substituted by alkoxyl groups or hydroxyalkoxyl groups or a combination of alkoxyl and hydroxyalkoxyl groups. The hydroxyalkoxyl groups are typically hydroxymethoxyl, hydroxyethoxyl and/or hydroxypropoxyl groups. Hydroxyethoxyl and/or hydroxypropoxyl groups are preferred. Typically one or two kinds of hydroxyalkoxyl groups are present in the esterified cellulose ether. Preferably a single kind of hydroxyalkoxyl group, more preferably hydroxypropoxyl, is present. The alkoxyl groups are typically methoxyl, ethoxyl and/or propoxyl groups. Methoxyl groups are preferred. Illustrative of the above-defined esterified cellulose ethers are esterified alkylcelluloses, such as esterified methylcelluloses, ethylcelluloses, and propylcelluloses; esterified hydroxyalkylcelluloses, such as esterified hydroxyethylcelluloses, hydroxypropylcelluloses, and hydroxybutylcelluloses; and esterified hydroxyalkyl alkylcelluloses, such as esterified hydroxyethyl methylcelluloses, hydroxymethyl ethylcelluloses, ethyl hydroxyethylcelluloses, hydroxypropyl methylcelluloses, hydroxypropyl ethylcelluloses, hydroxybutyl methylcelluloses, and hydroxybutyl ethylcelluloses; and those having two or more hydroxyalkyl groups, such as esterified hydroxyethylhydroxypropyl methylcelluloses. Most preferably, the esterified cellulose ether is an esterified hydroxyalkyl methylcellulose, such as an esterified hydroxypropyl methylcellulose.

The degree of the substitution of hydroxyl groups of the anhydroglucose units by hydroxyalkoxyl groups is expressed by the molar substitution of hydroxyalkoxyl groups, the MS(hydroxyalkoxyl). The MS(hydroxyalkoxyl) is the average number of moles of hydroxyalkoxyl groups per anhydroglucose unit in the esterified cellulose ether. It is to be understood that during the hydroxyalkylation reaction the hydroxyl group of a hydroxyalkoxyl group bound to the cellulose backbone can be further etherified by an alkylating agent, e.g. a methylating agent, and/or a hydroxyalkylating agent. Multiple subsequent hydroxyalkylation etherification reactions with respect to the same carbon atom position of an anhydroglucose unit yields a side chain, wherein multiple hydroxyalkoxyl groups are covalently bound to each other by ether bonds, each side chain as a whole forming a hydroxyalkoxyl substituent to the cellulose backbone.

The term "hydroxyalkoxyl groups" thus has to be interpreted in the context of the MS(hydroxyalkoxyl) as referring to the hydroxyalkoxyl groups as the constituting units of hydroxyalkoxyl substituents, which either comprise a single hydroxyalkoxyl group or a side chain as outlined above, wherein two or more hydroxyalkoxyl units are covalently bound to each other by ether bonding. Within this definition it is not important whether the terminal hydroxyl group of a hydroxyalkoxyl substituent is further alkylated or not; both alkylated and non-alkylated hydroxyalkoxyl substituents are included for the determination of MS(hydroxyalkoxyl). The esterified cellulose ether generally has a molar substitution of hydroxyalkoxyl groups of at least 0.05, preferably at least 0.08, more preferably at least 0.12, and most preferably at least 0.15. The degree of molar substitution is generally not more than 1.00, preferably not more than 0.90, more preferably not more than 0.70, and most preferably not more than 0.50.

The average number of hydroxyl groups substituted by alkoxyl groups, such as methoxyl groups, per anhydroglucose unit, is designated as the degree of substitution of alkoxyl groups, DS(alkoxyl). In the above-given definition of DS, the term "hydroxyl groups substituted by alkoxyl groups" is to be construed within the present invention to include not only alkylated hydroxyl groups directly bound to the carbon atoms of the cellulose backbone, but also alkylated hydroxyl groups of hydroxyalkoxyl substituents bound to the cellulose backbone. The esterified cellulose ethers preferably have a DS(alkoxyl) of at least 1.0, more preferably at least 1.1, even more preferably at least 1.2, most preferably at least 1.4, and particularly at least 1.6. The DS(alkoxyl) is preferably not more than 2.5, more preferably not more than 2.4, even more preferably not more than 2.2, and most not more than 2.05.

Most preferably the esterified cellulose ether is an esterified hydroxypropyl methylcellulose having a DS(methoxyl) within the ranges indicated above for DS(alkoxyl) and an MS(hydroxypropoxyl) within the ranges indicated above for MS(hydroxyalkoxyl).

The esterified cellulose ether(s) comprised in the capsules and capsule shells of the present invention has/have aliphatic monovalent acyl groups and groups of the formula —C(O)—R—COOH, wherein R is a divalent aliphatic or aromatic hydrocarbon group and wherein a part of the groups —C(O)—R—COOH are neutralized with an ammonium salt of carbonic acid, formic acid or acetic acid.

The aliphatic monovalent acyl groups are preferably selected from the group consisting of acetyl, propionyl, and butyryl, such as n-butyryl or i-butyryl.

Preferred groups of the formula —C(O)—R—COOH are —C(O)—CH$_2$—CH$_2$—COOH, —C(O)—CH=CH—COOH or —C(O)—C$_6$H$_4$—COOH. In the groups of formula —C(O)—C$_6$H$_4$—COOH the carbonyl group and the carboxylic group are preferably arranged in ortho-positions.

Preferred esterified cellulose ethers are
i) HPMCXY, wherein HPMC is hydroxypropyl methyl cellulose, X is A (acetate), or X is B (butyrate) or X is Pr (propionate) and Y is S (succinate), or Y is P (phthalate) or Y is M (maleate), such as hydroxypropyl methyl cellulose acetate phthalate (HPMCAP), hydroxypropyl methyl cellulose acetate maleate (HPMCAM), or hydroxypropyl methylcellulose acetate succinate (HPMCAS), or
ii) hydroxypropyl cellulose acetate succinate (HPCAS), hydroxybutyl methyl cellulose propionate succinate (HBMCPrS), hydroxyethyl hydroxypropyl cellulose propionate succinate (HEHPCPrS); and methyl cellulose acetate succinate (MCAS).

Hydroxypropyl methylcellulose acetate succinate (HPMCAS) is the most preferred esterified cellulose ether.

The esterified cellulose ether(s) comprised in the capsules and capsule shells generally has/have a degree of substitution of aliphatic monovalent acyl groups, such as acetyl, propionyl, or butyryl groups, of at least 0.05, more preferably at least 0.10, and most preferably at least 0.20. The degree of substitution of aliphatic monovalent acyl groups is generally up to 1.75, preferably up to 1.50, more preferably up to 1.25, and most preferably up to 1.00, or even only up to 0.65.

The esterified cellulose ether(s) comprised in the capsules and capsule shells of the invention generally has/have a degree of substitution of partially neutralized groups of formula —C(O)—R—COOH, such as partially neutralized succinoyl, of at least 0.05, preferably at least 0.10. The degree of substitution of partially neutralized groups of formula —C(O)—R—COOH generally is up to 1.6, preferably up to 1.30, more preferably up to 1.00, and most preferably up to 0.70 or even up to 0.60.

The sum of i) the degree of substitution of aliphatic monovalent acyl groups and ii) the degree of substitution of partially neutralized groups of formula —C(O)—R—COOH is generally at least 0.10, preferably at least 0.15, more preferably at least 0.20, most preferably at least 0.30, and particularly at least 0.40. The mentioned sum is generally no more than 2.0, preferably no more than 1.4, more preferably no more than 1.15, most preferably no more than 1.10 and particularly no more than 1.00.

The term "partially neutralized groups of formula —C(O)—R—COOH" as used herein means that a part of the groups —C(O)—R—COOH are neutralized with an ammonium salt of carbonic acid, formic acid or acetic acid. Preferred ammonium salts of carbonic acid, formic acid or acetic acid are ammonium carbonate, ammonium hydrogen carbonate, ammonium formate, or ammonium acetate. Ammonium hydrogen carbonate is most preferred. Most preferably, the esterified cellulose ether comprised in the capsules and capsule shells is hydroxypropyl methyl cellulose acetate succinate that is partially neutralized with ammonium carbonate or ammonium hydrogen carbonate.

The content of the acetate and succinate ester groups is determined according to "Hypromellose Acetate Succinate", United States Pharmacopeia and National Formulary, NF 29, pp. 1548-1550. Irrespective whether the succinate ester groups are present in the esterified cellulose ether in their acidic or neutralized form, the content of succinate ester groups is determined as succinoyl groups in their acidic form (—CO—CH$_2$—CH$_2$—COOH).

Reported values are corrected for volatiles (determined as described in section "loss on drying" in the above HPMCAS monograph). The method may be used in analogue manner to determine the content of propionyl, butyryl, phthalyl and other ester groups.

The content of ether groups in the esterified cellulose ether is determined in the same manner as described for "Hypromellose", United States Pharmacopeia and National Formulary, USP 35, pp 3467-3469.

The contents of ether and ester groups obtained by the above analyses are converted to DS and MS values of individual substituents according to the formulas below. The formulas may be used in analogue manner to determine the DS and MS of substituents of other cellulose ether esters.

$$\% \text{ cellulose backbone} = 100 - \left(\% \text{ MeO} * \frac{M(OCH_3) - M(OH)}{M(OCH_3)}\right) - \left(\% \text{ HPO} * \frac{M(OCH_2CH(OH)CH_3) - M(OH)}{M(OCH_2CH(OH)CH_3)}\right) - \left(\% \text{ Acetyl} * \frac{M(COCH_3) - M(H)}{M(COCH_3)}\right) - \left(\% \text{ Succinoyl} * \frac{M(COC_2H_4COOH) - M(H)}{M(COC_2H_4COOH)}\right)$$

$$DS(Me) = \frac{\frac{\% \text{ MeO}}{M(OCH_3)}}{\frac{\% \text{ cellulose backbone}}{M(AGU)}}$$

$$MS(HP) = \frac{\frac{\% \text{ HPO}}{M(HPO)}}{\frac{\% \text{ cellulose backbone}}{M(AGU)}}$$

$$DS(Acetyl) = \frac{\frac{\% \text{ Acetyl}}{M(Acetyl)}}{\frac{\% \text{ cellulose backbone}}{M(AGU)}}$$

$$DS(\text{Succinoyl}) = \frac{\frac{\% \text{ Succinoyl}}{M(\text{Succinoyl})}}{\frac{\% \text{ cellulose backbone}}{M(\text{AGU})}}$$

$M(MeO) = M(OCH_3) = 31.03 Da$ $M(HPO) = M(OCH_2CH(OH)CH_3) = 75.09 Da$ $M(\text{Acetyl}) = M(COCH_3) = 43.04 Da$ $M(\text{Succinoyl}) = M(COC_2H_4COOH) = 101.08 Da$ $M(AGU) = 162.14 Da$ $M(OH) = 17.008 Da$ $M(H) = 1.008 Da$ By convention, the weight percent is an average weight percentage based on the total weight of the cellulose repeat unit, including all substituents. The content of the methoxyl group is reported based on the mass of the methoxyl group (i.e., —$OCH_3$). The content of the hydroxyalkoxyl group is reported based on the mass of the hydroxyalkoxyl group (i.e., —O— alkylene-OH); such as hydroxypropoxyl (i.e., —O—$CH_2CH(CH_3)$—OH). The content of the aliphatic monovalent acyl groups is reported based on the mass of —C(O)—$R_1$ wherein $R_1$ is a monovalent aliphatic group, such as acetyl (—C(O)—$CH_3$). The content of the group of formula —C(O)—R—COOH is reported based on the mass of this group, such as the mass of succinoyl groups (i.e., —C(O)—$CH_2$—$CH_2$—COOH).

The esterified cellulose ether(s) comprised in the capsules and capsule shells of the present invention generally has/have a viscosity of at least 1.2 mPa·s, preferably least 1.8 mPa·s, and more preferably least 2.4 mPa·s, and generally no more than 200 mPa·s, preferably no more than 100 mPa·s, more preferably no more than 50 mPa·s, and most preferably no more than 30 mPa·s, measured as a 2.0 weight percent solution of the esterified cellulose ether in 0.43 weight-% aqueous NaOH at 20° C. according to "Hypromellose Acetate Succinate, United States Pharmacopia and National Formulary, NF 29, pp. 1548-1550".

The polymeric capsule shell of the present invention can comprise one or more of the esterified cellulose ethers which have groups of formula —C(O)—R—COOH that are partially neutralized with an ammonium salt of carbonic acid, formic acid or acetic acid as described above. However, it is a great advantage of the present invention that the total weight of these esterified cellulose ethers in the capsule shells of the present invention is at least 80 percent, preferably at least 85 percent, even more preferably at least 90 percent, and often even at least 94 percent, based on of the total polymer weight in the capsule shell. The total amount of these esterified cellulose ethers in the capsule shells is up to 100 percent or up to 98 percent, or in some cases up to 96 percent, based on the total polymer weight in the capsule shell.

In one embodiment the polymeric capsule shell of the present invention comprises a polymeric capsule forming aid, typically only a small amount, such as 2 percent or more, or 4 percent or more, based on the total polymer weight in the capsule shell. However, it is a great advantage of the present invention that the capsule shell only comprises up to 20 percent, preferably up to 15 percent, more preferably up to 10 percent, and most preferably only up to 6 percent of a polymeric capsule forming aid, if any, based on the total polymer weight in the capsule shell. The amount of the polymeric capsule forming aid(s) is small enough not to affect the enteric properties of the capsule shell. Exemplary of polymeric capsule forming aids are cellulose ethers, such as carboxy methylcellulose, hydroxypropyl cellulose, ethyl cellulose, methylcellulose, hydroxypropylmethylcellulose (HPMC), e.g. HPMC types 2910, 2906 and/or 2208 as defined in USP30-NF25; gelatin, pullulan, non-enteric starch derivatives, such as hydroxypropyl starch; polyvinyl acetate derivatives (PVAP), and mixtures thereof. Exemplary of other polymeric capsule forming aids are gelling agents. Gelling agents are typically used in the "cold-pin method" for producing capsules, as described further below. Typical gelling agents are carrageenan, pectin, or gellan gum. The total amount of polymeric capsule forming aids including gelling agents are within the ranges indicated above. Surprisingly, no polymeric capsule forming aid is needed to obtain capsules and capsule shells of the present invention of excellent quality.

In another embodiment the polymeric capsule shell of the present invention comprises up to 7 percent, preferably up to 5 percent, more preferably up to 3 percent, and most preferably only up to 2.5 percent of a non-polymeric plasticizer, based on the weight of the esterified cellulose ether. The lower limit of plasticizer is 0, 1.0 or 2.0 percent, based on the weight of the esterified cellulose ether. Surprisingly, no plasticizer is needed to obtain capsules and capsule shells of the present invention of excellent quality. Exemplary of non-polymeric plasticizer are phthalic esters, such as dimethyl-, diethyl-, and diisopropyl-phthalate; citric esters, such as triethyl-, tributyl-, acetyltriethyl- and acetyltributyl-citrate; phosphoric esters, such as triethyl-, tricresyl-, and triphenyl-phosphate; alkyl lactate; glycol esters; glycerol and glycerol esters, such as glycerol triacetate also known as triacetine; sucrose esters; oils and fatty acid esters; butyl stearate; dibutyl sebacate; dibutyl tartrate; diisobutyl adipate, tributyrin; propylene glycol; sorbitan monoesters; fatty acid esters; glycol ricinoleate; triethyl citrate (TEC); acetyl trialkyl citrate; talc; and mixtures thereof.

The polymeric capsule shell of the present invention may comprise optional adjuvants, such as one or more gelling agents, coloring agents, pigments, opacifiers, flavor and taste improvers, antioxidants, and any combination thereof. Optional additives are preferably pharmaceutically acceptable. The amount of the optional additives is typically up 40 percent, more typically up to 20 percent, and most typically up to 10 percent, based on the total weight of the capsule shell, provided that the weight of the above-described one or more esterified cellulose ethers amounts to at least 80 percent of the total polymer weight in the capsule shell and further provided that the capsule shell does not comprise more than 7 weight percent of a non-polymeric plasticizer, based on the weight of the esterified cellulose ether.

The polymeric capsule shell of the present invention is prepared from an aqueous composition which comprises (A) at least one esterified cellulose ether comprising aliphatic monovalent acyl groups and groups of the formula —C(O)—R—COOH as described further above, wherein at least a part of the groups —C(O)—R—COOH are neutralized with an ammonium salt of carbonic acid, formic acid or acetic acid, and (B) from 0 to 7 weight percent of a non-polymeric plasticizer, based on the weight of the esterified cellulose ether, wherein the weight of said at least one esterified cellulose ether is at least 80 percent of the total polymer weight in the aqueous composition.

The aqueous composition typically comprises at least 2 percent, preferably at least 5 percent, and more preferably at least 10 percent or even at least 12 percent esterified cellulose ether(s), based on the total weight of the aqueous composition. The aqueous composition typically comprises up to 35 percent or up to 30 percent, or more typically up to 25 percent esterified cellulose ether(s), based on the total weight of the aqueous composition. The aqueous composition of the present invention can comprise one, two or more types of the above-described esterified cellulose ethers, but their total amount should be in the ranges indicated above. Optional additives, such as capsule forming aid(s), non-polymeric plasticizer(s), other optional additives and their amounts are those described above for the capsule shells. Their useful weight ranges can be calculated from the ranges described for the capsule shells and the weight percentages of esterified cellulose ether(s) and aqueous diluent in the aqueous composition disclosed herein.

In the aqueous composition used for preparing the polymeric capsule shell of the present invention at least a part of the groups —C(O)—R—COOH in the esterified cellulose ether(s) are neutralized with an ammonium salt of carbonic acid, formic acid or acetic acid, which means that the groups of the formula —C(O)—R—COOH can be partially or fully neutralized with an ammonium salt of carbonic acid, formic acid or acetic acid. Preferably the groups —C(O)—R—COOH are fully or partially neutralized to such extent with an ammonium salt of carbonic acid, formic acid or acetic acid that the esterified cellulose ether is soluble in the aqueous composition used for preparing the polymeric capsule shell. Using an aqueous solution of the esterified cellulose ether for preparing the polymeric capsule shell provides many advantages. For example, aqueous solutions are typically easier to be handled than solutions based on organic solvents. Moreover, when the esterified cellulose ether is soluble in the aqueous composition, there is no need to use the high amounts of dispersant that are needed for the dispersions disclosed in International Patent Application WO 2013/164121. In the aqueous composition used for preparing the polymeric capsule shells of the present invention the weight of dispersant typically is not more than 5 percent, more typically not more than 2 percent, and even more typically not more than 1 percent, based on the total weight of the esterified cellulose ether(s). Most typically the aqueous composition used for preparing the polymeric capsule shell of the present invention does not comprise a dispersant.

In the aqueous composition used for preparing the polymeric capsule shell of the present invention preferably at least 50 mol percent, more preferably at least 75 mol percent, most preferably at least 85 mol percent, and particularly at least 87 mol percent of the groups of formula —C(O)—R—COOH in the esterified cellulose ether(s) are neutralized with an ammonium salt of carbonic acid, formic acid or acetic acid. Preferably up to 100 mol percent, more preferably up to 95 mol percent, and most preferably up to 93 mol percent, of the groups of formula —C(O)—R—COOH are neutralized with an ammonium salt of carbonic acid, formic acid or acetic acid. It may be desirable to incorporate a higher amount of ammonium salt of carbonic acid, formic acid or acetic acid into the aqueous composition than is needed to achieve 100 percent neutralization of the groups of formula —C(O)—R—COOH. Preferably, ammonium salt of carbonic acid, formic acid or acetic acid is incorporated in such amount into the aqueous composition that the resulting pH of the composition is at least 5.5, more preferably at least 5.8, and most preferably at least 6.3; and preferably up to 7.5, more preferably up to 7.2, and most preferably up to 7.0, measured at 23° C. To achieve such degree of neutralization, typically at least 0.5 mmols, preferably at least 0.8 mmols, and more preferably at least 0.9 mmols, and typically up to 2.0 mmols, preferably up to 1.5 mmols, and more preferably up to 1.2 mmols of ammonium salt of carbonic acid, formic acid or acetic acid are incorporated into the aqueous composition per mmole of groups of formula —C(O)—R—COOH that are comprised in the aqueous composition. During the production of the capsule shells, particularly during their drying at elevated temperature, some or nearly all of the neutralized groups —C(O)—R—COO$^-$NH$_4^+$ in the esterified cellulose ether are transformed back into their acidic form such that in the produced polymeric capsule shell only a part, and sometimes even only a small number, of the groups —C(O)—R—COOH in the esterified cellulose ether remain neutralized with an ammonium salt of carbonic acid, formic acid or acetic acid:

In the capsules and capsule shells of the present invention, particularly in the dried capsules and capsule shells of the present invention, typically 3 mol percent or more, more typically 10 mol percent or more, and most typically 20 mol percent or more, but typically not more than 55 mol percent, more typically not more than 45 mol percent, and most typically not more than 40 mol percent of the groups of formula —C(O)—R—COOH in the esterified cellulose ether(s) are still neutralized with an ammonium salt of carbonic acid, formic acid or acetic acid.

The aqueous composition that is used for producing a capsule of the present invention comprises an aqueous diluent. The aqueous diluent is water, optionally mixed with a minor amount of an organic solvent. The aqueous diluent preferably consists of 50 to 100 weight percent, more preferably 65 to 100 weight percent, and most preferably 75 to 100 weight percent of water and preferably 0 to 50 weight percent, more preferably 0 to 35 weight percent, and most preferably 0 to 25 weight percent of an organic solvent, based on the total weight of water and the organic solvent. Useful organic solvents are polar organic solvents having one or more heteroatoms, such as oxygen, nitrogen or halogen like chlorine. More preferred organic solvents are alcohols, preferably monofunctional alcohols, such as methanol, ethanol, isopropanol or n-propanol; ethers, such as tetrahydrofuran, ketones, such as acetone; methyl ethyl ketone, or methyl isobutyl ketone; acetates, such as ethyl acetate; halogenated hydrocarbons, such as methylene chloride; or nitriles, such as acetonitrile. Preferably the aqueous composition of the present invention comprises water alone as aqueous diluent. The amount of the aqueous diluent is typically at least 60 percent, more typically at least 70 percent, and most typically at least 75 percent, based on the total weight of the aqueous composition. The amount of the aqueous diluent is typically no more than 95 percent, more typically no more than 90 percent, and most typically no more than 87 percent, based on the total weight of the aqueous composition.

UK Patent Application GB 2 353 215 discloses the use of a buffering agent with high vapor pressure, such as ammonium hydrogen carbonate, to increase the pH of water to 7.8 and to dissolve enteric polymers, such as cellulose acetate phthalate (CAP), hydroxypropyl methylcellulose phthalate (HPMCP), hydroxypropyl methylcellulose acetate succinate (HPMCAS) or polymethacrylic acid esters. The solution is used for coating tablets. Upon drying of the aqueous coating solution, the buffer evaporates and changes the polymer to its non-ionized from. The use of the solution for producing free-standing films or for producing capsules is not disclosed in GB 2 353 215. Moreover, the coating solution comprises a large amount of the plasticizer triacetine. When HPMCAS is used as enteric polymer, the amount of the plasticizer triacetine is as high as 20 percent, based on the weight of HPMCAS.

In view of the teaching of GB 2 353 215 it is highly surprisingly that capsules of high quality can be produced from an aqueous composition which comprises (A) at least one esterified cellulose ether comprising groups of the formula —C(O)—R—COOH, wherein at least a part of the groups —C(O)—R—COOH are neutralized with an ammonium salt of carbonic acid, formic acid or acetic acid, and (B) from 0 to 7 weight percent of a non-polymeric plasticizer, based on the weight of the esterified cellulose ether, wherein said at least one esterified cellulose ether amounts to at least 80 percent of the total polymer weight in the aqueous composition. Preferably capsules shells for enteric use are produced, i.e., capsules shells that are dissolved in the intestinal canals to release the active ingredient like a drug contained in the capsules. Preferably hard capsules are produced from the described aqueous composition.

It is even more surprising that capsules of high quality can be produced from such aqueous composition in a simple dipping process. Accordingly, in yet another aspect of the invention such aqueous composition is used for the manufacture of capsules shells in a process which comprises the steps of dipping molding pins into the aqueous composition, forming a film on said molding pins by withdrawing said pins from said aqueous composition, and drying the film on the molding pins.

According to a preferred embodiment the process for producing capsule shells comprises the steps of providing the aqueous composition as described above, pre-heating molding pins to a temperature higher than the aqueous composition, dipping the pre-heated molding pins into the aqueous composition, forming a film on said molding pins by withdrawing said pins from said aqueous composition, and drying the film on the molding pins. The method is generally known as "hot-pin method" and typically characterized by 3 major factors. The first factor is the temperature of the aqueous composition. The temperature of the aqueous composition determines the fluidity of the aqueous composition coated on the molding pin. The temperature of the aqueous composition typically is at least 5° C., more typically at least 10° C., and typically up to 30° C., more typically up to 25° C. The aqueous composition is typically maintained at a temperature that is less than the gelation temperature therefor by 2 to 12° C., for example, by 2 to 10° C. The second factor is the temperature of the molding pin. The temperature of the preheated molding pin is an important factor to determine the film thickness of the capsule or capsule shell, respectively. The film thickness of the capsule or capsule shell, respectively, may decrease as the temperature decreases, and the film thickness of the capsule or capsule shell, respectively, may increase as the temperature increases. The molding pin is typically maintained at a temperature that is greater than the gelation temperature for the aqueous composition by 10 to 75° C., preferably by 20 to 70° C., even though the temperature of the molding pin may vary according to the size of the capsule. The temperature of the molding pin typically is at least 40° C., more typically at least 50° C., and typically up to 95° C., more typically up to 90° C. The third factor is the drying temperature. The drying temperature generally controls the fluidity of the aqueous composition coated on the molding pin. In general, the aqueous composition that is coated on the molding pin and that is to be dried is transferred to a drying device. In this regard, at the beginning of the drying, the aqueous composition is maintained at a temperature that is equal to or greater than the gelation temperature for the aqueous composition for a predetermined period of time to completely fix the aqueous composition on the molding pin to prevent the aqueous composition from flowing. A typical drying temperature is 60° C. or more, preferably 65° C. or more, and more preferably 70° C. or more. Typical drying temperatures are up to 85° C., preferably up to 80° C., and more preferably up to 75° C. A first drying period generally is in the range of 1 to 240 minutes, for example 60 to 150 minutes. Then, the molding pin is generally maintained in a drying device at a lower temperature, typically at 20 to 40° C., for a second drying period to completely dry the capsule, e.g., for 30 to 60 minutes.

Another method for the manufacture of capsules is the "cold-pin method". In this method the above-described aqueous composition which comprises an esterified cellulose ether that is at least partially neutralized with an ammonium salt of carbonic acid, formic acid or acetic acid as described above and additionally a gelling agent such as carrageenan, pectin, gellan gum, or another sequestering agent or gelling aid, such as potassium, magnesium, ammonium, or calcium ions. In the cold-pin method the temperature of the molding pin typically is at least 15° C., more typically at least 20° C., and typically up to 22° C., more typically up to 25° C. Most preferably the molding pins are kept at room temperature. The molding pins are dipped into the aqueous composition that is pre-heated to a temperature higher than the molding pins. The aqueous composition is generally maintained at a temperature above its gelation temperature. The temperature of the aqueous composition typically is at least 40° C., more typically at least 45° C., and typically up to 48° C., more typically up to 50° C. The dipping pins are withdrawn from the aqueous composition and a film is obtained on the dipping pins, and the film is dried on the dipping pins to obtain molded capsule shells on the pins. A typical drying temperature is 30° C. or more, preferably 35° C. or more, and more preferably 40° C. or more. Typical drying temperatures are up to 80° C., preferably up to 70° C., and more preferably up to 65° C.

The capsule shells can take the form of caps and bodies, which are then removed from the pins. Caps are mated with bodies to form capsules.

Without wanting to be bound to the theory, Applicant believes that residual byproduct of the neutralization reaction, such as $H_2CO_3$, acts as plasticizer via associating with the succinic groups —C(O)—R—COOH when the aqueous composition is contacted with preheated molding pins that have a temperature higher than the aqueous composition or when the aqueous composition is pre-heated before it is contacted with cold pins and when the aqueous composition forms a film on the molding pins during the dipping process. When the aqueous composition is dried on the molding pins, residual ammonium salt(s) of carbonic acid, formic acid or acetic acid typically decompose at the drying temperature. For example, ammonium hydrogen carbonate ($NH_4HCO_3$) decomposes to $NH_3$, $CO_2$ and $H_2O$ at about 60° C. or more at atmospheric pressure. Without wanting to be bound to the theory, Applicant believes that the evaporation of $NH_3$ and $CO_2$ in addition to $H_2O$ contributes to setting of the film on the molding pins resulting in a homogeneous film. The dried capsule shells and capsules do not comprise substantial amounts of residual alkaline material. This is a great advantage as compared to the capsules disclosed in WO 2013/164121. The capsules disclosed in WO 2013/164121 comprise alkaline material that does not evaporate upon drying and/or that comprises a large amount of non-polymeric plasticizer, such as triacetine.

Moreover, during drying of the capsule shells on the molding pins at elevated temperature, some or nearly all of the neutralized groups —C(O)—R—COO$^-$NH$_4^+$ in the esterified cellulose ether are transformed back into their acidic form:

—C(O)—R—COO$^-$NH$_4^+$ ↔ —C(O)—R—COOH+ NH$_3$(↑).

Esterified cellulose ethers that comprise acidic groups —C(O)—R—COOH have enteric properties, i.e., they are substantially insoluble in gastric fluid and rapidly dissolve in intestinal fluid. Accordingly, the polymeric capsule shells and capsules of the present invention are particularly useful for enteric use, i.e., capsules shells that are dissolved in the intestinal canals to release the active ingredient like a drug contained in the capsules. Hard capsule shells are preferred.

Another aspect of the invention are capsules, particularly hard capsules, that comprise a capsule shell of the invention and that further comprise one or more drugs and/or one or more nutritional or food supplements, such as one or more vitamins, herbals or mineral supplements. The drug, nutritional or food supplement is surrounded by the shell material of the present invention. The hard capsules are preferably two-piece hard capsules. The capsule shells in the form of caps and bodies can be prepared as described above. One or more drugs and/or one or more nutritional or food supplements can be placed into capsules bodies, caps can be mated with bodies to form capsules and the formed capsules can be sealed according to methods known in the art.

Some embodiments of the invention will now be described in detail in the following Examples.

EXAMPLES

Unless otherwise mentioned, all parts and percentages are by weight. In the Examples the following test procedures are used.

Viscosity of Hydroxypropyl Methyl Cellulose Acetate Succinate (HPMCAS)

A 2.0% by weight solution of the HPMCAS in 0.43 wt. % aqueous NaOH was prepared as described in "Hypromellose Acetate Succinate, United States Pharmacopia and National Formulary, NF 29, pp. 1548-1550, followed by an Ubbelohde viscosity measurement at 20° C. according to DIN 51562-1:1999-01 (January 1999).

Acid Dissociation Constant (pKa) of HPMCAS

The pKa of HPMCAS was measured with the following titration method. About 0.4 g of a HPMCAS sample was accurately weighed into a 200 mL polyethylene titration beaker and diluted with about 60 mL of ultra-pure water purified by a Milli-Q process. The solution was then stirred on a magnetic stir plate using a Teflon stir bar and 0.1M NaOH was added until the solution pH was increased to pH 7-8. The temperature of the solution was kept at 23° C. After dissolution, the sample was titrated on a Metrohm 904 Titrando using 0.1M HCl with continuous stirring. A titration curve was generated and pKa was determined by determining the pH value at half of the volume at equivalent point.

$$pH - \log\left(\frac{[-CO-CH2-CH2-COO^-]}{[-CO-CH2-CH2-COOH]}\right) = pKa$$

Content of Ether and Ester Groups of HPMCAS

The content of ether groups in HPMCAS was determined in the same manner as described for "Hypromellose", United States Pharmacopeia and National Formulary, USP 35, pp 3467-3469.

The ester substitution with acetyl groups (—CO—CH$_3$) and the ester substitution with succinoyl groups (—CO—CH$_2$—CH$_2$—COOH) and neutralized succinoyl groups were determined according to Hypromellose Acetate Succinate, United States Pharmacopia and National Formulary, NF 29, pp. 1548-1550". Reported values for ester substitution were corrected for volatiles (determined as described in section "loss on drying" in the above HPMCAS monograph). The DS$_{succinoyl}$ is determined as succinoyl groups in their acidic form (—CO—CH$_2$—CH$_2$—COOH).

DS(succinoyl)=DS(—CO—CH2-CH2-COO$^-$)+DS(—CO—CH2-CH2-COOH)

Apparent Viscosity of the Aqueous Composition

The apparent viscosity of the aqueous solution comprising HPMCAS was measured at various temperatures according to a temperature sweep experiment performed with a Anton Paar MCR 301 rheometer with a CC-27 cup geometry and a 4-blade vane geometry ST26-4V-20 over a temperature range of 10 to 50° C. with a heating rate of 3° C./min and a constant speed of the vane geometry of 40 rpm and a measurement point duration of 0.2721 min. Prior to this temperature sweep testing the material was treated with a SpeedMixer™ DAC 150.1 FV (FlackTek Inc.) at 2300 rpm for 1 min to remove air bubbles. A sample volume of 20 ml was used for these measurements. The samples had been stored at room temperature prior to the viscosity measurement.

Degree of Neutralization of the Succinoyl Groups in the Dried Capsule Shells

The mol percentage of neutralized succinoyl groups, based on the total number of succinoyl groups, in the dried capsule shells can be detected as the residual moles of NH$_4^+$, which is equivalent to residual moles of N in the capsule shell. The elemental analysis of N in the capsule shell was performed on a Flash 2000 Organic Elemental Analyzer (Thermo Fisher Scientific).

$$\frac{\text{N detected in weight \%} * \text{molecular weight of AGU in } \frac{g}{mol}}{DS(\text{succinoyl}) * 14 \text{ g/mol}} =$$

mol precentage of neutralized succinoyl groups

Degree of Neutralization of the Succinoyl Groups in the Aqueous Solution Used for Producing the Capsule Shells The mol percentage of neutralized succinoyl groups, based on the total number of succinoyl groups, in the aqueous solution was calculated from the pH value of the solution, measured at 23° C., and the pKa of the HPMCAS according to the following formula:

$$100 \times \frac{10^{(pH-pKa)}}{1 + 10^{(pH-pKa)}} = \text{mol precentage of neutralized succinoyl groups.}$$

Film Strength of Capsule Material

Film puncture strength and distance were measured on a texture analyzer (Model TA.XT2, Texture Technologies, Scarsdale, N.Y.) equipped with a 25-kg load cell. A 7-mm-diameter, 45-mm-long probe (model TA-57R) and film extensibility fixture (TA-10855) with 9-mm round openings (modified from original 10-mm openings) were used to conduct the testing. The film thickness was recorded before each sample was placed in the fixture. The fixture was aligned under the probe, and the films were compressed with 10 g of force at a speed of 2.1 mm/s until failure. Five runs were performed on each specimen; the average film rupture strength that is normalized by film thickness and elongation at break were recorded.

Example 1

Preparation of Capsule Shells

An aqueous solution was prepared from 15% hydroxypropyl methyl cellulose acetate succinate (HPMCAS), 1.1% $NH_4HCO_3$, and 83.9% deionized water, based on the total weight of the aqueous composition. The aqueous composition contained 0.89 mmols of added $NH_4HCO_3$ per mmol of succinoyl groups ($—CO—CH_2—CH_2—COOH$).

HPMCAS was used that had
23.5% methoxyl groups ($DS_{methoxyl}$=1.93),
7.3% hydroxypropoxyl groups ($MS_{hydroxypropoxyl}$=
9.8% acetyl groups ($DS_{acetyl}$=0.58),
10.5% succinoyl groups ($DS_{succinoyl}$=0.26),
a molecular weight of AGU (anhydroglucose unit) of 254 g/mol,
a pKa of 5.1, and
a viscosity of 2.9 mPa·s, measured as a 2.0% by weight solution of the HPMCAS in 0.43 wt. % aqueous NaOH.

The aqueous solution was prepared by quickly dispersing HPMCAS powder into an 800-mL beaker equipped with a three-blade shaft containing deionized water of about 23° C. The rotation rate during the addition of powder was set to maintain a vortex that continuously drew the powder into the water (>400 rpm). After HPMCAS powder addition, the $NH_4HCO_3$ salt was added slowly to the dispersion and allowed to stir at 400 rpm for 3 hours at room temperature to reach a transparent aqueous solution. No adjuvants like capsule forming aids, gelling agents or plasticizers were added. The final pH was measured to be about 5.9. The viscosity of the solution satisfied the standard capsule manufacturing requirements as shown in Table 1 below. The resulting degree of neutralization of succinoyl groups in the solution was 86 mol percent, i.e., 86 mol percent of the groups $—CO—CH_2—CH_2—COOH$ in the HPMCAS comprised in the aqueous solution were neutralized and present as $—CO—CH_2—CH_2—COO^-NH_4^+$ groups.

TABLE 1

| Temperature | Viscosity |
|---|---|
| 10° C. | 2730 mPa · s |
| 15° C. | 2740 mPa · s |
| 20° C. | 2545 mPa · s |
| 25° C. | 2300 mPa · s |
| 30° C. | 2040 mPa · s |
| 35° C. | 1800 mPa · s |
| 40° C. | 1635 mPa · s |
| 45° C. | 1655 mPa · s |

Figure 1:
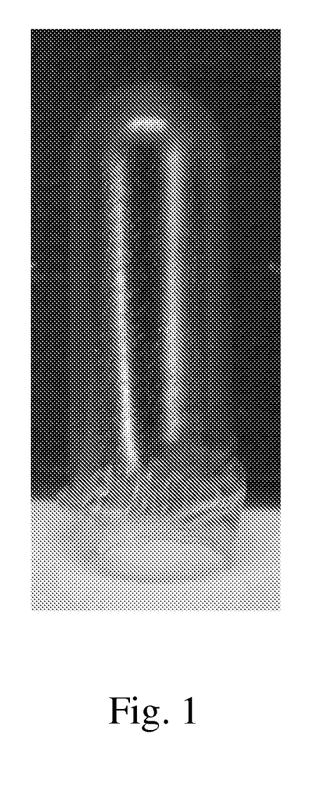
FIG. 1 represents a photograph of a polymeric capsule shell of the present invention.

Capsules shells were prepared by pre-heating molding pins to a temperature of 80° C. and dipping them into the transparent aqueous solution that was kept at a temperature of 20° C. The pins were then withdrawn from the aqueous solution and a film was formed on the molding pins. The films on the molding pins were dried in a drying chamber having a humidity of 83% and a temperature of 80° C. for 120 min. Capsule bodies and caps were produced. The capsule caps had an average thickness at the tips of 9 mil (0.23 mm) and an average thickness at the sidewalls of 8 mil (0.20 mm). The capsule bodies had an average thickness at the tips of 8.5 mil (0.22 mm) and an average thickness at the sidewalls of 8 mil (0.20 mm). Capsule shells of excellent clarity and film quality were obtained. FIG. 1 represents a photograph of a polymeric capsule shell produced according to Example 1.

The resulting degree of neutralization of succinoyl groups was 29 mol percent, i.e., 29 mol percent of the groups $—CO—CH_2—CH_2—COOH$ in the HPMCAS comprised in the dried capsule shells were neutralized and present as $—CO—CH_2—CH_2—COO^-NH_4^+$ groups.

Preparation of Capsules

Capsule bodies were filled with 150 mg of the drug Metformin and 160 mg of hydroxypropyl methylcellulose (HPMC) that comprises 19-24% methoxyl groups and 7-12 wt. % hydroxypropoxyl groups and that has an apparent viscosity of 3000-5600 mPa·s, measured as a 2 wt. % solution in water at 20° C. The HPMC is commercially available from The Dow Chemical Company under the trademark Methocel K4M.

The capsule bodies were mated with capsule caps and sealed by applying a thin layer of a 10 weight percent solution of the HPMCAS of Example 1 in acetone at the cap and body interface followed by drying at 25° C. overnight.

Figure 2:
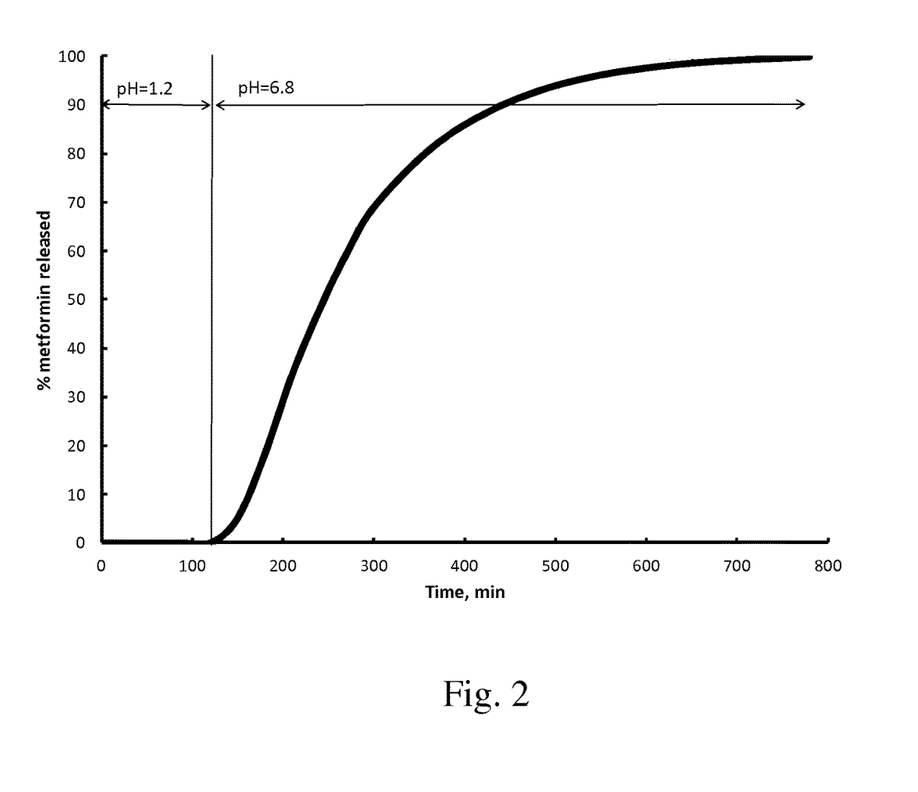
FIGS. 2 and 3 each illustrate the release of a drug from a capsule of the present invention after the drug has been filled into a capsule shell of the present invention and the filled and sealed capsule is placed into an aqueous solution buffered at a pH of 1.2 or 6.8 respectively.

The dissolution behavior of thus prepared capsules was measured according to method A of delayed-release dosage forms in U.S. Pharmacopeia (USP 37) General Chapter <711>. Sealed capsules were first immersed in 750 ml of 0.1 N HCl buffer of a pH=1.2 at 37±0.5° C. and the % released Metformin was measured. Even after 120 min. no measurable percentage of the drug Metformin was released. The buffer was then adjusted to a pH of 6.8 by adding 250 ml of 0.2 M tribasic sodium phosphate that had been equilibrated to 37±0.5° C. The % released Metformin from the sealed capsules was then measured. The Metformin release profile at pH 1.2 and 6.8 is illustrated in FIG. 2, which illustrates the enteric properties of the capsules of the present invention.

Figure 3:
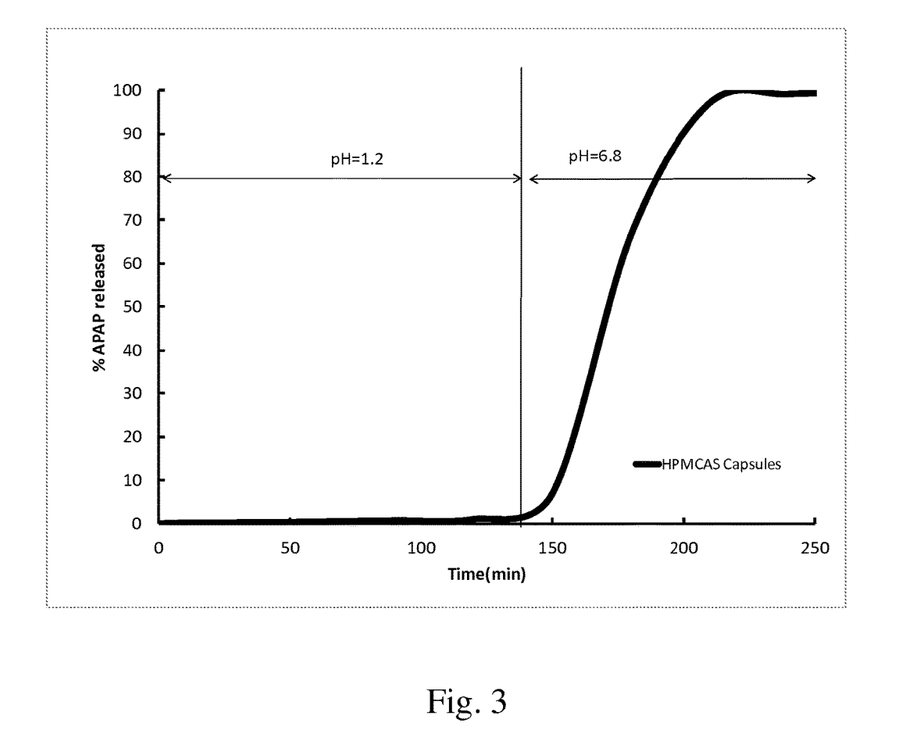

Other capsule bodies were filled with 200 mg of the drug acetaminophen (APAP), the capsule bodies were mated with capsuled caps and sealed as described above. The dissolution behavior of thus prepared capsules was measured as described above for the capsules filled with Metformin. The APAP release profile at pH 1.2 and 6.8 is illustrated in in FIG. 3, which also illustrates the enteric properties of the capsules of the present invention.

Preparation of Free-Standing Films for Determining the Film Strength of the Capsule Material Films of about 8 inch×14 inch (20 cm×35 cm) were cast on Teflon™ substrates at room temperature using a 50 mil (1.27 mm) gap film casting bar. The casted films were allowed to dry in air in a constant temperature room (22° C. and 50% room humidity) for two days, were removed and annealed for an additional day before any film properties were measured.

The film strength prepared from the aqueous solution of Example 1 was 2332 g/mil (=91827 g/mm).

Comparative Example A

An aqueous solution was prepared from 14.7% hydroxypropyl methyl cellulose phthalate (HPMCP 50), 3.0% $NH_4HCO_3$, and 82.3% deionized water, based on the total weight of the aqueous composition. The minimum amount of $NH_4HCO_3$ was chosen to bring HPMCP into solution. The HPMCP was commercially available from Cole-Parmer as HPMCP 50 that comprises 20-24 wt. % methoxyl groups, 6-10 wt. % hydroxypropoxyl groups, 21-27 wt. % of phthalyl groups; and a viscosity of 44-66 mPa·s, measured as a 10 wt. % solution in a mixed solvent of Methanol and Methylene Chloride (50/50 vol/vol) at 20° C. (USP/NF method) from Acros Organics N.V.

The solution was prepared as described above for Example 1. Films were prepared as described for Example 1 above. The film strength of the films was 1318 g/mil (=51875 g/mm).

The comparison between Example 1 and Comparative Example A illustrates that the capsule material of the present invention has a considerably higher film strength than that of Comparative Example A.

What is claimed is:

1. A polymeric capsule shell comprising
   (A) a hydroxypropyl methyl cellulose acetate succinate, wherein a part of the succinoyl groups are neutralized with an ammonium salt of carbonic acid, formic acid or acetic acid,
   (B) from 0 to 7 weight percent of a non-polymeric plasticizer, based on the weight of the hydroxypropyl methyl cellulose acetate succinate, and
   (C) from 0 to 1 weight percent of a dispersant, based on the total weight of the hydroxypropyl methyl cellulose acetate succinate,
   wherein the weight of said hydroxypropyl methyl cellulose acetate succinate is at least 80 percent of the total polymer weight in the capsule shell.

2. The capsule shell of claim 1 wherein the weight of said hydroxypropyl methyl cellulose acetate succinate is at least 85 percent of the total polymer weight in the capsule shell.

3. The capsule shell of claim 1 comprising hydroxypropyl methyl cellulose acetate succinate that is partially neutralized with ammonium carbonate or ammonium hydrogen carbonate.

4. The capsule shell of claim 1 additionally comprising at least one adjuvant selected from the group consisting of gelling agents, coloring agents, pigments, opacifiers, flavor and taste improvers, and antioxidants.

5. The capsule shell of claim 1 being a hard capsule shell.

6. A capsule comprising a capsule shell of claim 1 and further comprising a drug or a nutritional or food supplement or a combination thereof.

7. A polymeric capsule shell prepared from an aqueous composition comprising
   (A) a hydroxypropyl methyl cellulose acetate succinate, wherein at least 50 mol percent of the succinoyl groups are neutralized with an ammonium salt of carbonic acid, formic acid or acetic acid such that the hydroxypropyl methyl cellulose acetate succinate is soluble in the aqueous composition,
   (B) from 0 to 7 weight percent of a non-polymeric plasticizer, based on the weight of the hydroxypropyl methyl cellulose acetate succinate, and
   (C) from 0 to 1 weight percent of a dispersant, based on the total weight of the hydroxypropyl methyl cellulose acetate succinate,
   wherein the weight of said hydroxypropyl methyl cellulose acetate succinate is at least 80 percent of the total polymer weight in the aqueous composition.

8. The polymeric capsule shell of claim 7 prepared from an aqueous composition comprising a hydroxypropyl methyl cellulose acetate succinate, wherein at least 75 mole percent of the succinoyl groups are neutralized with an ammonium salt of carbonic acid, formic acid or acetic acid.

9. A process for producing polymeric capsule shells comprising the steps of
   providing an aqueous composition comprising (A) a hydroxypropyl methyl cellulose acetate succinate, wherein the succinoyl groups are fully or partially neutralized to such extent with an ammonium salt of carbonic acid, formic acid or acetic acid such that at least 50 mol percent of the succinoyl groups are neutralized and that the hydroxypropyl methyl cellulose acetate succinate is soluble in the aqueous composition, (B) from 0 to 7 weight percent of a non-polymeric plasticizer, based on the weight of the hydroxypropyl methyl cellulose acetate succinate, and (C) from 0 to 1 weight percent of a dispersant, based on the total weight of the hydroxypropyl methyl cellulose acetate succinate, wherein the weight of said hydroxypropyl methyl cellulose acetate succinate is at least 80 percent of the total polymer weight in the aqueous composition,
   dipping molding pins into the aqueous composition,
   forming a film on said molding pins by withdrawing said pins from said aqueous composition, and
   drying the film on the molding pins.

10. The process of claim 9 which comprises the steps of
    pre-heating molding pins to a temperature higher than the aqueous composition,
    dipping the pre-heated molding pins into the aqueous composition,
    forming a film on said molding pins by withdrawing said pins from said aqueous composition, and
    drying the film on the molding pins.

11. The process of claim 10 wherein the film on the molding pins is dried at a temperature of at least 60° C. to partially remove the ammonium salt of carbonic acid, formic acid or acetic acid or its decomposition products from the produced capsule shells.

12. The process of claim 9 which comprises the steps of
    providing an aqueous composition which additionally comprises a gelling agent,
    pre-heating the aqueous composition to a temperature higher than the molding pins,
    dipping the molding pins into the pre-heated aqueous composition,
    forming a film on said molding pins by withdrawing said pins from said aqueous composition, and
    drying the film on the molding pins.

13. The process of claim 12 wherein the film on the molding pins is dried at a temperature of at least 60° C. to partially remove the ammonium salt of carbonic acid, formic acid or acetic acid or its decomposition products from the produced capsule shells.

14. The process of claim 9 wherein the weight of the hydroxypropyl methyl cellulose acetate succinate is at least 85 percent of the total polymer weight in the capsule shell.

15. The process of claim 9 wherein at least 75 mole percent of the succinoyl groups are neutralized with an ammonium salt of carbonic acid, formic acid or acetic acid.

16. The process of claim 9 wherein the pH of the aqueous composition is at least 5.5.

* * * * *